United States Patent [19]

Moon et al.

[11] 4,113,956

[45] Sep. 12, 1978

[54] THIENYL PYRAZOLE AMIDES

[75] Inventors: Malcolm W. Moon; Gabriel Kornis, both of Kalamazoo, Mich.

[73] Assignee: The Upjohn Company, Kalamazoo, Mich.

[21] Appl. No.: 846,159

[22] Filed: Oct. 27, 1977

Related U.S. Application Data

[60] Division of Ser. No. 686,548, May 14, 1976, Pat. No. 4,072,498, which is a continuation-in-part of Ser. No. 524,231, Nov. 15, 1974, abandoned.

[51] Int. Cl.$^2$ .................. C07D 409/04; C07D 409/14
[52] U.S. Cl. ........................ 548/374; 548/369; 548/372; 260/293.7; 260/293.6
[58] Field of Search ............... 548/374, 372, 369; 260/293.7, 293.6

[56] References Cited

U.S. PATENT DOCUMENTS 3,957,480  5/1976  Kornis .......................... 260/293.7
3,960,836  6/1976  Gutowski ...................... 548/374

FOREIGN PATENT DOCUMENTS 1,298,642  12/1972  United Kingdom.
1,373,212  11/1974  United Kingdom.

OTHER PUBLICATIONS

Jones et al., J. Org. Chem., 1954, vol. 19, pp. 1428–1434.
Kornis et al., Chem. Absts., 1971, vol. 75, 129808x.
Talbert et al., Chem. Absts., 1972, vol. 76, 122780u.

Primary Examiner—Natalie Trousof
Assistant Examiner—Natalia Harkaway
Attorney, Agent, or Firm—Bruce Stein; John J. Killinger

[57] ABSTRACT

The present invention discloses amides and thioamides substituted in the α or β position with substituted pyrazoles which are useful as herbicides.

10 Claims, No Drawings

THIENYL PYRAZOLE AMIDES

CROSS REFERENCE TO RELATED APPLICATION

This is a division of application Ser. No. 686,548, filed May 14, 1976 now U.S. Pat. No. 4,072,498 issued Feb. 7, 1978 which is a continuation in part of application Ser. No. 524,231, filed Nov. 15, 1974, now abandoned.

The present invention relates to thienyl pyrazole amides, for which the essential material constituting a disclosure thereof is incorporated by reference here from U.S. patent application Ser. No. 686,548, filed May 14, 1976, now U.S. Pat. No. 4,072,498.

We claim:

1. A compound of the formula:

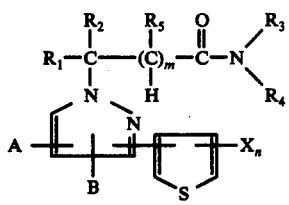

III where $R_1$ is hydrogen, alkyl of 1 to 7 carbon atoms, inclusive, haloalkyl of 1 to 7 carbon atoms, inclusive, phenyl, benzyl or cycloalkyl of 3 to 6 carbon atoms, inclusive, with the proviso that when $R_1$ is benzyl or cycloalkyl $m = 0$; $R_2$ and $R_5$ are the same or different and are hydrogen, halogen, alkyl of 1 to 6 carbom atoms, inclusive, haloalkyl of 1 to 6 carbon atoms, inclusive, or phenyl; $R_1$ and $R_2$ together with the attached carbon atom can be cycloalkyl of 3 to 6 carbon atoms, inclusive, when $m = 0$; $m$ is 0 or 1 provided that when $m = 0$, $R_1$ is not hydrogen and when $m = 1$ at least one of $R_2$ or $R_5$ is hydrogen; $R_3$ is hydrogen, alkyl of from 1 to 8 carbon atoms, inclusive, phenyl or benzyl; $R_4$ is hydrogen or alkyl of from 1 to 6 carbon atoms, inclusive, and $R_3$ and $R_4$ can be joined together to form a heterocyclic ring selected from the group consisting of pyrrolidine, or piperidine; A and B are the same or different and are hydrogen, alkyl of from 1 to 6 carbon atoms, inclusive, phenyl, halogen, cyano, haloalkyl of 1 to 6 carbon atoms, inclusive, alkoxy or alkylthio in which the alkyl group is from 1 to 3 carbon atoms, inclusive, or trifluoromethyl and when adjacent can be joined to form a ring of from 5 to 7 carbon atoms, inclusive; where X is halogen, nitro, cyano, acetyl, dimethylcarbamoyl, alkyl, haloalkyl, alkoxy or carboalkoxy in which the alkyl group is from 1 to 3 carbon atoms, inclusive, phenyl, benzyl, 2-phenylethyl and $n$ is 0, 1, or 2 or an acid addition salt thereof.

2. A compound according to claim 1 which is N,N,α-trimethyl-3-(2-thienyl)pyrazole-1-acetamide.

3. A compound according to claim 1 which is N,N,α-trimethyl-5-(2-thienyl)pyrazole-1-acetamide.

4. A compound according to claim 1 which is N,N,α,4-tetramethyl-3-(2-thienyl)pyrazole-1-acetamide.

5. A compound according to claim 1 which is N,N,α,4-tetramethyl-5-(2-thienyl)pyrazole-1-acetamide.

6. A compound according to claim 1 which is α-ethyl-N,N,4-trimethyl-3-(2-thienyl)pyrazole-1-acetamide.

7. A compound according to claim 1 which is α-ethyl-N,N,4-trimethyl-5-(2-thienyl)pyrazole-1-acetamide.

8. A compound according to claim 1 which is N,N,α,4-tetramethyl-3-(5-chloro-2-thienyl)pyrazole-1-acetamide.

9. A compound according to claim 1 which is N,N,4-trimethyl-α-propyl-3-(2-thienyl)pyrazole-1-acetamide.

10. A compound according to claim 1 which is N,N,α,α,4-pentamethyl-3-(2-thienyl)pyrazole-1-acetamide.